(12) United States Patent
Yao et al.

(10) Patent No.: US 10,111,876 B2
(45) Date of Patent: Oct. 30, 2018

(54) ALK KINASE INHIBITOR AND ITS USE

(71) Applicant: Macau University of Science and Technology, Taipa (MO)

(72) Inventors: Xiao-Jun Yao, Taipa (MO); Elaine Lai-Han Leung, Taipa (MO); Lian-Xiang Luo, Taipa (MO); Liang Liu, Taipa (MO)

(73) Assignee: MACAU UNIVERSITY OF SCIENCE AND TECHNOLOGY, Taipa (MO)

( * ) Notice: Subject to any disclaimer, the term of this patent is extended or adjusted under 35 U.S.C. 154(b) by 0 days.

(21) Appl. No.: 15/239,288

(22) Filed: Aug. 17, 2016

(65) Prior Publication Data

US 2018/0050037 A1 Feb. 22, 2018

(51) Int. Cl.
*A61K 31/519* (2006.01)

(52) U.S. Cl.
CPC .................................. *A61K 31/519* (2013.01)

(58) Field of Classification Search
None
See application file for complete search history.

(56) References Cited

FOREIGN PATENT DOCUMENTS

WO    WO 2008155468 A1 * 12/2008 ........... A61K 31/519

OTHER PUBLICATIONS

McDuff, F. et al., PLoS ONE 2011 vol. 6 pp. 1-11.*
Yuan, Y. et al, J. Hematol Oncol 2011 vol. 4 pp. 1-14.*
Vousden, K. et al., Nat. Rev. Mol. Cell Biol., 2007, vol. 8, pp. 275-283.*
Wang, J.-P. et al., Toxicol. Appl. Pharmacol. 2013 vol. 273, pp. 110-120.*
Takeuchi, K. et al. RET, ROS1 and ALK fusions in lung cancer. Nature medicine18, 378-381 (2012).
Davare, M.A. et al. Foretinib is a potent inhibitor of oncogenic ROS1 fusion proteins. Proceedings of the National Academy of Sciences of the United States of America110, 19519-19524 (2013).
Sang, J. et al. Targeted inhibition of the molecular chaperone Hsp90 overcomes ALK inhibitor resistance in non-small cell lung cancer. Cancer discovery3, 430-443 (2013).
Friboulet, L. et al. The ALK inhibitor ceritinib overcomes crizotinib resistance in non-small cell lung cancer. Cancer discovery4, 662-673 (2014).
Gandhi, L. & Janne, P.A. Crizotinib for ALK-rearranged non-small cell lung cancer: a new targeted therapy for a new target. Clinical cancer research : an official journal of the American Association for Cancer Research18, 3737-3742 (2012).
Zou, H.Y. et al. PF-06463922 is a potent and selective next-generation ROS1/ALK inhibitor capable of blocking crizotinib-resistant ROS1 mutations. Proceedings of the National Academy of Sciences of the United States of America112, 3493-3498 (2015).
Med, S.T. Escaping ALK inhibition_ mechanisms of and strategies to overcome resistance. Lovly CM, Pao W4 (2012).
Katayama, R. et al. Therapeutic strategies to overcome crizotinib resistance in non-small cell lung cancers harboring the fusion oncogene EML4-ALK. Proceedings of the National Academy of Sciences of the United States of America108, 7535-7540 (2011).

* cited by examiner

*Primary Examiner* — Heidi Reese
(74) *Attorney, Agent, or Firm* — Renner Kenner Greive Bobak Taylor & Weber

(57) ABSTRACT

A compound for treating a disease, in particular cancer like non-small cell lung cancer, exceptionally inhibits activity of oncogenic ALK kinase. Compositions, particularly pharmaceutical compositions, are provided comprising this compound. Methods for targeting cancer cells harboring an abnormality in the ALK gene are also The compound for treating a disease has certain structural elements, namely a tricyclic, more specifically heterocyclic, backbone as the core part of the compound at least one highly electronegative atom in form of a tertiary amine attached to the backbone via an at most 6-membered linking group with a terminal highly electronegative atom in form of a nitrogen as secondary amine, and a further hydrophobic moiety fused to the backbone. The structural components allow for an advantageous interaction with the ALK kinase domain. The compound therefor represents a highly promising treatment option for patients in particular those bearing ALK-dependent non-small cell lung cancer.

5 Claims, 11 Drawing Sheets

ALK KINASE INHIBITOR AND ITS USE

TECHNICAL FIELD

The present invention relates to a compound that can, in particular, inhibit ALK kinase activity for treating a disease like cancer such as ALK-dependent non-small cell lung cancer as well as compositions such as pharmaceutical compositions comprising said compound. The present invention, in particular, provides a method of treating a subject such as a human suffering from a disease, in particular from cancer such as non-small cell lung cancer and for inhibiting ALK kinase activity in cancer cells such as non-small cell lung cancer cells.

BACKGROUND OF INVENTION

Receptor tyrosine kinases are mediators of extracellular signals through activation of downstream signaling pathways including ERK, AKT and/or STAT3 cascades to control cell growth, proliferation, survival and motility pathways. In particular, chromosome rearrangements, gene amplification, and point mutations in respective genes contribute to and/or result in abnormal and constitutive receptor tyrosine kinase activation which is, in turn, responsible for initiation and progression of many cancers including non-small cell lung cancer (NSCLC).

A receptor tyrosine kinase identified in cancers such as NSCLC is the anaplastic lymphoma kinase (ALK), wherein chromosome rearrangements of the ALK gene have been identified among which is as most common form the echinoderm microtubule-associated protein-like 4 (EML4)-ALK, i.e. comprising portions of the EML4 gene and the ALK gene, wherein several variants of EML4-ALK gene fusions have been identified. Furthermore, additional fusion partners besides EML4 have been identified and, additionally, ALK activating point mutations and presence of additional gene copies have been observed in cancers activating the signaling pathways downstream to ALK.

In the majority of cases, ALK chromosome rearrangements are non-overlapping with other gene abnormalities found in NSCLC (e.g. Gandhi, L. and Jänne, P. A., Clinical cancer research: an official journal of the American Association for Cancer Research, 2012, 18, 3737-3742). ALK oncogenic chromosome rearrangements, thus, define a unique molecular subset of NSCLC patients. Approximately 3-7% of NSCLCs harbor the ALK chromosome rearrangement (Takeuchi, K. et al., Nature medicine, 2012, 18, 378-381). The constitutive kinase activity associated with ALK chromosome rearrangements seems to play a particular role in cell growth, survival, and motility pathways in NSCLC (Davare, M. A. et al., Proceedings of the National Academy of Sciences of the United States of America, 2013, 110, 19519-19524, Sang, J. et al., Cancer discovery, 2013, 3, 430-443). ALK, thus, serves as a potent oncogenic "driver," wherein cancers with chromosome rearrangements of ALK seem to be particular sensitive to ALK tyrosine kinase inhibition (Friboulet, L. et al., Cancer discovery, 2014, 4, 662-673).

The first generation ALK/ROS1/Met inhibitor crizotinib has demonstrated promising clinical benefit in NSCLC harboring chromosome rearrangements of ALK and has been approved by the Food and the Drug Administration for treatment of such NSCLC in 2011 (Gandhi, L. and Jänne, P. A., Clinical cancer research: an official journal of the American Association for Cancer Research, 2012, 18, 3737-3742). Although many patients with NSCLC harboring chromosome rearrangements of ALK derive substantial clinical benefit from crizotinib, durable responses to crizotinib therapy have been hampered because of acquired resistances as seen with most kinase inhibitors (Zou, H. Y. et al., Proceedings of the National Academy of Sciences of the United States of America, 2015, 112, 3493-3498, Lovly C. M., Pao, W., Science Translational Medicine, 2012, 4, 120). Accordingly, patients who responded to crizotinib will eventually experience disease progression despite continued treatment. Strategies to overcome said acquired resistance have not yet been established (Katayama, R. et al., Proceedings of the National Academy of Sciences of the United States of America, 2011, 108, 7535-7540).

Thus, further potent receptor tyrosine kinase inhibitors for cancer therapy have to be identified. Accordingly, there is a strong need for new compounds which are able to target receptor tyrosine kinases and sufficiently inhibit the kinase activity, in particular ALK kinase activity, which compounds can, thus, be used for cancer therapy, in particular for treatment of NSCLC.

SUMMARY OF INVENTION

The first aspect of the present invention relates to a method of treating a disease, in particular cancer, preferably lung cancer such as NSCLC, by a compound of Formula (I) in a subject in need thereof, in particular a human.

Namely the method of treating a subject suffering from a disease like cancer comprises administering an effective amount of a compound having the structure of Formula (I) or a pharmaceutically acceptable salt, solvate or anhydrate thereof to the subject:

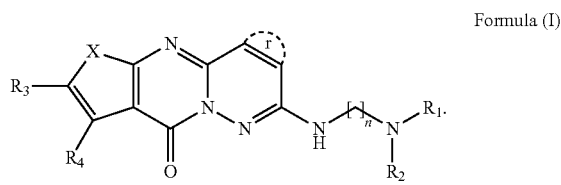

Formula (I)

Wherein $R^1$, $R^2$, $R^3$ and $R^4$ are each independently selected from hydrogen or a $C_1$-$C_3$-alkyl. r represents an optionally substituted $C_5$-$C_8$-aryl or optionally substituted $C_5$-$C_8$-heteroaryl. n is an integer of from 1 to 5. X is a heteroatom and selected from N, O or S.

Hence, the compound of the present invention comprises certain structural elements, namely a tricyclic, more specifically a heterocyclic backbone as core part of the compound, at least one group with a highly electronegative atom in form of a tertiary amine attached to the backbone via an at most 6-membered linking group with a terminal highly electronegative atom in form of a nitrogen as secondary amine, and a further hydrophobic moiety in form of an optionally substituted $C_5$-$C_8$-aryl or $C_5$-$C_8$-heteroaryl fused to the backbone. The inventors found that having such structural features makes the compound especially suitable for inhibiting ALK kinase activity, in particular ALK fusion kinase activity.

It is expected that the compound of Formula (I) is suitable to inhibit to c-ros oncogene 1 (ROS1) and respective ROS1 fusion kinases, as well, as ALK and ROS1 kinase are reported to share 77% amino acid identity within the ATP binding site and to share more than 64% overall sequence homology in the kinase domain and about 84% within the ATP binding site, respectively. Rearrangements of ROS1 gene were observed in several cancers including NSCLC while defining a distinct subgroup of NSCLC. I.e. the compound of Formula (I) can be used for treating ROS1-dependent cancer like ROS1-dependent NSCLC and inhibit ROS1 kinase activity including ROS1 fusion kinase activity, respectively.

In particular, the compound of Formula (IV) and (V), respectively, proved to be an especially potent inhibitor of ALK kinase activity inhibiting cell viability, colony formation and inducing cell apoptosis in NSCLC cells with abnormality in the ALK gene, namely which harbor an EML4-ALK chromosome rearrangement. The antitumor efficacy proved to be dose dependent and strongly correlated to the suppression in ALK phosphorylation as well as its downstream signaling molecules ERK1/2, STAT3 and AKT. Thus, the compound of the present invention has most preferably the structure of Formula (IV) or is a pharmaceutically acceptable salt, solvate or anhydrate of the compound of Formula (IV) which also encompasses the base and any protonated form, in particular the protonated form of Formula (V):

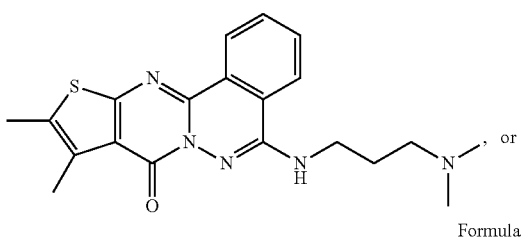

Formula (IV)

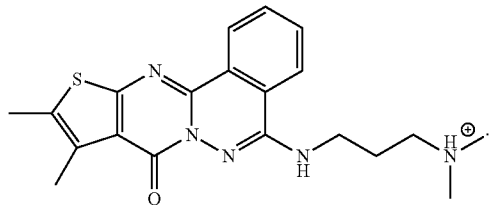

Formula (V)

In still another aspect, the present invention refers to a method of inhibiting ALK kinase activity, in particular ALK fusion kinase activity, in cancer cells by a compound of Formula (I) in a subject in need thereof, i.e. comprising administering an effective amount of the compound of Formula (I), in particular a compound of Formula (IV) and (V), respectively, to a subject suffering from cancer, in particular lung cancer like NSCLC. The cancer is in particular ALK-dependent NSCLC.

According to the invention is also the compound of Formula (I) such as Formula (IV) and (V), respectively, for use as a medicament, preferably for use in the treatment of a disease, in particular cancer such as NSCLC like ALK-dependent NSCLC. Furthermore, the invention refers to the use of the compound of Formula (I) such as Formula (IV) and (V), respectively, for preparing a medicament for treatment of a disease, in particular cancer such as NSCLC like ALK-dependent NSCLC.

Another aspect of the present invention relates to a composition comprising the compound of Formula (I) or a salt, solvate or anhydrate thereof:

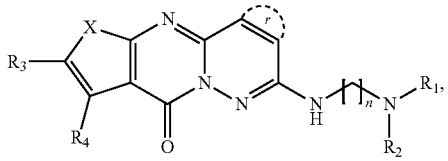

Formula (I)

wherein $R^1$ to $R^4$, n, r and X are as defined above including preferred embodiments as mentioned above. In particular the composition is a pharmaceutical composition comprising the compound of Formula (I) or a pharmaceutically acceptable salt, solvate or anhydrate thereof. Said pharmaceutical composition further comprises pharmaceutically acceptable excipients and may additionally contain further active ingredients, in particular therapeutic compounds for treating cancer such as NSCLC. The present invention also refers to the use of the composition, in particular the pharmaceutical composition, for inhibiting ALK kinase activity, in particular ALK fusion kinase activity, such as for suppressing phosphorylation of ALK kinase, in particular ALK fusion kinase, and/or inhibiting the anti-apoptotic and growth signaling downstream to ALK kinase, in particular ALK fusion kinase.

The present invention, in another aspect, refers to a method for targeting cancer cells harboring an abnormality in ALK gene, in particular an abnormality in ALK gene resulting from an ALK chromosome rearrangement such as EML4-ALK associated with the expression of at least one EML4-ALK fusion kinase. Said method of the present invention comprises the step of contacting said cells with a compound of Formula (I) or a salt, solvate or anhydrate thereof:

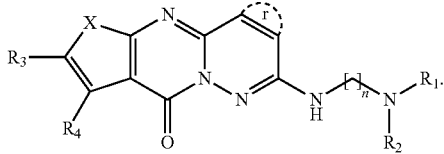

Formula (I)

$R^1$ to $R^4$, n, r and X are as defined above including preferred embodiments as mentioned above. The cancer cells can be present in a sample such as a tissue sample of cancer cells and the cancer, respectively, in particular from a human.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF DRAWINGS

FIG. 2A shows a graph obtained with the LanthaScreen® Eu Kinase Binding Assay for assessing the binding capacity between crizotinib and ALK. FIG. 2B shows a graph obtained with the LanthaScreen® Eu Kinase Binding Assay for assessing the binding capacity between the compound of Formula (V) and ALK.

FIG. 3A shows the cell viability of H2228 cells after 72 hours treatment with the compound of Formula (V). FIG. 3B shows the cell viability of normal lung cells CCD19 after 72 hours treatment with the compound of Formula (V).

FIG. 4A shows a Flow Cytometry pattern of H2228 cells having been treated with 2.5 µM crizotinib. FIG. 4B shows a Flow Cytometry pattern of the control group of H2228 cells. FIG. 4C shows a Flow Cytometry pattern of H2228 cells having been treated with 2.5 µM of the compound of Formula (V). FIG. 4D shows a Flow Cytometry pattern of H2228 cells having been treated with 5 µM of the compound of Formula (V). FIG. 4E shows a Flow Cytometry pattern of H2228 cells having been treated with 10 µM of the compound of Formula (V).

FIG. 5A refers to the formation of H2228 cell colonies after treatment with 2.5 µM crizotinib. FIG. 5B refers to the formation of H2228 cell colonies in the control group. FIG. 5C refers to the formation of H2228 cell colonies after treatment with 2.5 µM of the compound of Formula (V). FIG. 5D refers to the formation of H2228 cell colonies after treatment with 5 µM of the compound of Formula (V). FIG. 5E refers to the formation of H2228 cell colonies after treatment with 10 µM of the compound of Formula (V).

DETAILED DESCRIPTION OF INVENTION

Figure 1:
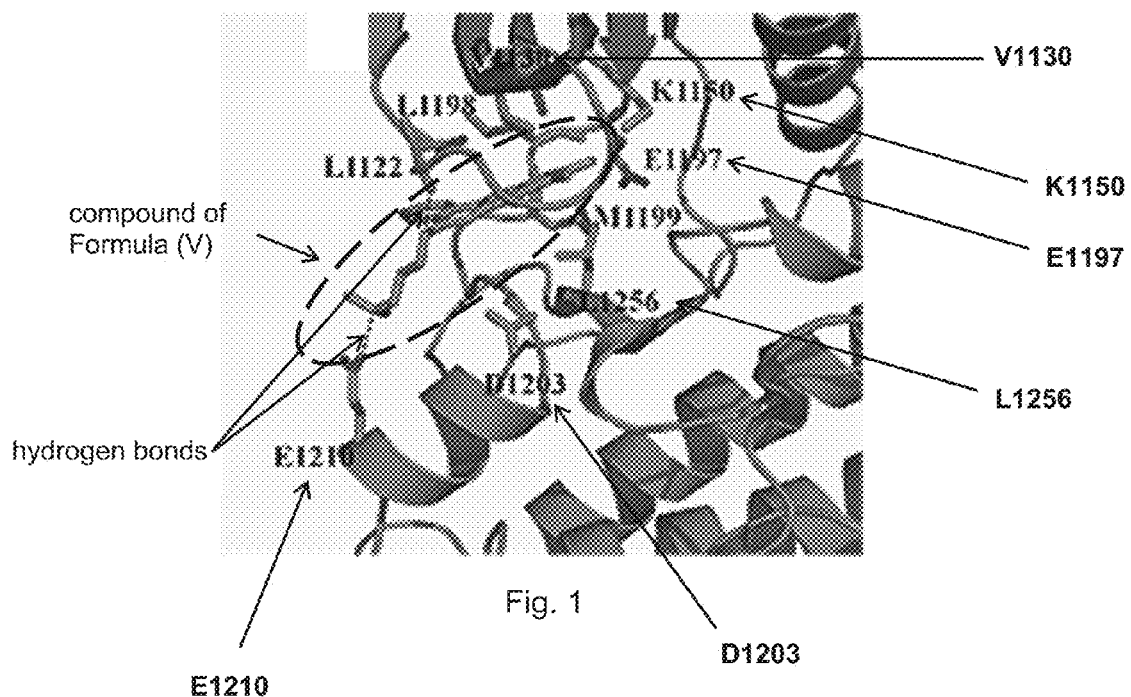
FIG. 1 shows a 3D schematic representation of the binding mode between the compound of Formula (V) and the predicted binding pocket of the ALK kinase domain. Hydrogen bonds are indicated.
Figure 2A:
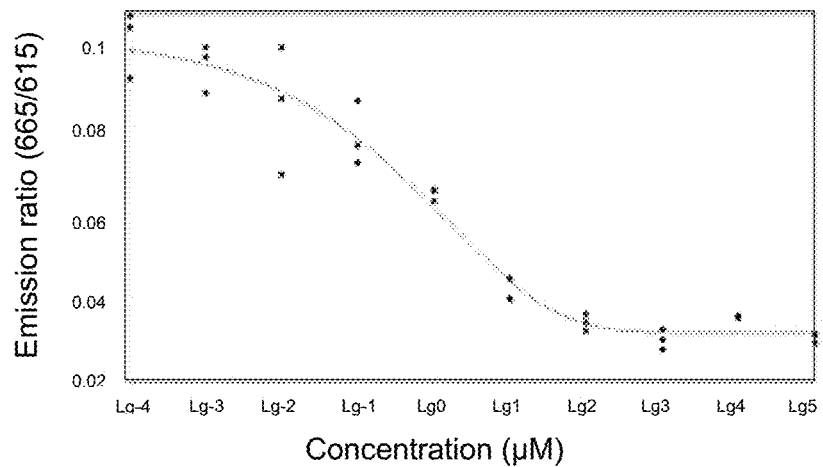
FIGS. 2A and 2B show the binding capacity of the compound of Formula (V), crizotinib and ALK.
Figure 2B:
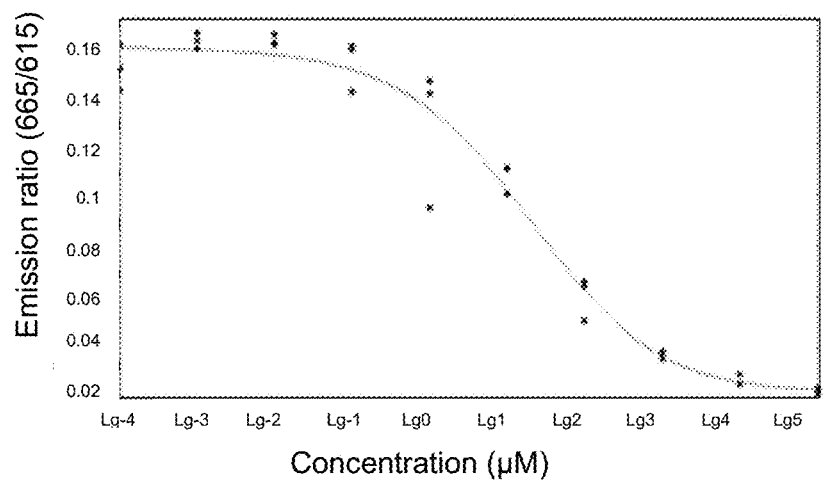

Unless otherwise defined, all technical terms used herein have the same meaning as commonly understood by one skilled in the art to which the invention belongs.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element.

The present invention provides a compound for use in a method for treating a disease, in particular cancer, in a subject in need thereof. More specifically, the present invention, in a first aspect, refers to a method of treating a subject suffering from a disease, in particular cancer, comprising administering an effective amount of a compound to the subject. The cancer is, in particular, NSCLC such as NSCLC adenocarcinoma, in particular ALK-dependent NSCLC like ALK-dependent NSCLC adenocarcinoma.

The term "ALK-dependent" (or ALK-positive) as used herein refers to a cancer with cancer cells harboring an abnormality in the ALK gene. The abnormality in the ALK gene preferably results from one or more of: an ALK chromosome rearrangement, additional gene copies of the ALK gene or point mutations in the ALK gene itself in particular point mutations in the tyrosine kinase domain, i.e. mutations affecting only one or very few nucleotides in the ALK gene sequence. "ALK chromosome rearrangement" used herein refers to a type of chromosome abnormality such as due to interchromosomal translocation or intrachromosomal deletion, inversion or duplication involving the ALK gene, which results in the creation of fusion genes of the rearrangement partner and the ALK gene usually associated with the expression of an ALK fusion kinase containing the whole kinase domain of ALK wild-type kinase. For example, ALK chromosome rearrangement EML4-ALK comprises portions of the echinoderm microtubule-associated protein-like 4 (EML4) gene with the ALK gene associated with the expression of a respective EML4-ALK fusion kinase.

Most preferably, said abnormality in the ALK gene is an ALK chromosome rearrangement, which means an ALK gene fusion. Hence, most preferably "ALK-dependent" means cancer with cancer cells harboring an abnormality in the ALK gene, which abnormality in the ALK gene results from an ALK chromosome rearrangement. The chromosome rearrangement is, preferably, selected from one or more of EML4-ALK, KIF5B (Kinesin Family Member 5B)-ALK, KLC1 (kinesin light chain 1)-ALK, PTPN3 (protein tyrosine phosphatase, nonreceptor type 3)-ALK, STRN (striatin)-ALK and TFG (TRK-fused gene)-ALK, most preferably the chromosome rearrangement is or is at least EML4-ALK. This also includes respective variants of the aforementioned chromosome rearrangements in particular variants of EML4-ALK chromosome rearrangements which include, for example, EML4-ALK, E13;A20 (variant 1), EML4-ALK, E20;A20 (variant 2), EML4-ALK, E6a/b;A20 (variant 3a/b), EML4-ALK, E14;A20 (variant 4), EML4-ALK, E2a/b;A20 (variant 5a/b), EML4-ALK, E13b;A20 (variant 6), EML4-ALK, E14;A20 (variant 7), EML4-ALK, E15;A20 (variant "V4"), EML4-ALK, E17;A20 and EML4-ALK, E18;A20 (variant "V5"). Variants of KIF5B-ALK include, for example, KIF5B-ALK, K17;A20 or KIF5B-ALK, K24;A20.

Preferably, the abnormality in the ALK gene is associated with an expression, namely at least a detectable expression, of an ALK kinase, if the ALK kinase is not expressed in non-cancerous cells of the same cell or tissue type without abnormality in the ALK gene, otherwise an increase in the expression and/or an increase in the activity of the ALK kinase compared to non-cancerous cells of the same cell or tissue type without abnormality in the ALK gene. In particular, said abnormality in the ALK gene is associated with either the expression of an ALK fusion kinase or an increased expression and/or an increased activity of ALK wild-type kinase.

Especially preferably, said abnormality in ALK gene is an ALK chromosome rearrangement associated with the expression of at least one ALK fusion kinase in particular selected from the group consisting of EML4-ALK, KIF5B-ALK, KLC1-ALK, PTPN3-ALK, STRN-ALK and TFG-ALK. Most preferably selected from of at least one EML4-ALK fusion kinase in particular at least one EML4-ALK fusion kinase resulting from a variant of EML4-ALK chromosome rearrangement including EML4-ALK, E13;A20 (variant 1), EML4-ALK, E20;A20 (variant 2), EML4-ALK, E6a/b;A20 (variant 3a/b), EML4-ALK, E14;A20 (variant 4), EML4-ALK, E2a/b;A20 (variant 5a/b), EML4-ALK, E13b; A20 (variant 6), EML4-ALK, E14;A20 (variant 7), EML4-ALK, E15;A20 (variant "V4"), EML4-ALK, E17;A20 and EML4-ALK, E18;A20 (variant "V5"), in particular from EML4-ALK, E13;A20 (variant 1), EML4-ALK, E20;A20 (variant 2) or EML4-ALK, E6a/b;A20 (variant 3a/b).

In all these fusion kinases, the ALK kinase domain of ALK wild-type kinase is fully retained. I.e. ALK-dependent cancer preferably has cancer cells with a detectable expression of at least one ALK fusion kinase, respectively, as a result of the fusion between the ALK gene and another gene.

An "increased expression" of ALK kinase means an expression at least 5% and preferably at least 10% higher and in particular at least 30% higher than in a control group, i.e. non-cancerous cells of the same cell or tissue type without abnormality in the ALK gene. The skilled person is aware of suitable methods for determining the ALK kinase expression like with PCR and Western blotting. An "increased activity" can, for example, be measured by means of the activation of the signaling pathways downstream to ALK like the amount of phosphorylated ALK, phosphorylated STAT3, phosphorylated ERK1/2 and/or phosphorylated AKT which can be determined with Western Blotting or respective assays. The activity can, for example, considered for being increased in case of an at least 5%, preferably at least 10% and more preferably at least 30% increase in the amount of phosphorylated ALK or phosphorylated peptides or proteins like STAT3, AKT or ERK1/2.

ALK wild-type kinase, its structure as well as ALK chromosome rearrangements and resulting ALK fusion kinases are known to the skilled person. "ALK wild-type kinase" (or -protein) generally refers to the respective full length protein with the sequence as encoded in normal (healthy) cells or tissue, namely non-cancerous cells or tissue without ALK chromosome rearrangements or other abnormalities in the ALK gene. In contrast, "ALK fusion kinase" refers to the fusion protein expressed after ALK chromosome rearrangement(s), in which at least the kinase domain of the ALK wild-type protein fused to all or a portion of another protein and polypeptide, respectively. The term "ALK kinase" as used herein covers wild-type kinase as well as fusion kinase.

Whether a cancer or cancer cells are ALK-dependent can be confirmed by respective molecular biological methods, wherein several methods are known to the skilled person (e.g. Takeuchi, K. et al., Nature medicine, 2012, 18, 378-381). Commonly used and suitable methods especially include fluorescence in situ hybridization (FISH), immunohistochemistry (IHC) and quantitative real-time reverse transcription-PCR (qRT-PCR) assays or chromogenic in situ hybridization (CISH). I.e. "ALK-dependent cancer" or "abnormality in the ALK gene" is in particular considered for being fulfilled when at least one of the methods selected from FISH, IHC, CISH or qRT-PCR assay reveals an ALK chromosome rearrangement. The same is true with regard to the specific type of ALK chromosome rearrangement, for which methods, in particular fusion partner specific assays, are known to the skilled person, as well. In particular, a cancer or cancer cells are ALK-dependent, if after carrying out the Vysis ALK Break Apart FISH Probe Kit assay the cancer cells comprised in a sample are considered for being positive (re-arranged).

The cancer is preferably a lung cancer, in particular an ALK-dependent lung cancer. Preferably, the lung cancer is NSCLC. Hence, in especially preferred embodiments of the present invention, the disease is NSCLC, in particular an ALK-dependent NSCLC such as NSCLC adenocarcinoma. The disease is, in particular, an ALK-dependent NSCLC having an abnormality in ALK gene resulting from an ALK chromosome rearrangement, which preferably includes ALK chromosome rearrangement with the generation of at least one EML4-ALK fusion kinase, i.e. at least one fusion kinase resulting from a EML4-ALK chromosome rearrangement including respective variants, in particular at least one chromosome rearrangement and/or fusion kinase resulting from EML4-ALK, E13;A20 (variant 1), EML4-ALK, E20; A20 (variant 2) or EML4-ALK, E6a/b;A20 (variant 3a/b).

The terms "cancer" and "cancerous" refer to or describe a physiological condition in subjects in which a population of cells are characterized by unregulated cell growth. The term "tumor" simply refers to a mass being of benign (generally harmless) or malignant (cancerous) growth.

The method of the present invention comprises administering an effective amount of a compound or a pharmaceutically acceptable salt, solvate or anhydrate thereof to a subject. The subject can be a human or animal, in particular the subject is a human. In preferred embodiments of the present invention, the subject is a mammal and most preferably a human having ALK-dependent NSCLC such as ALK-dependent NSCLC adenocarcinoma. The compound of the present invention has a structure of Formula (I):

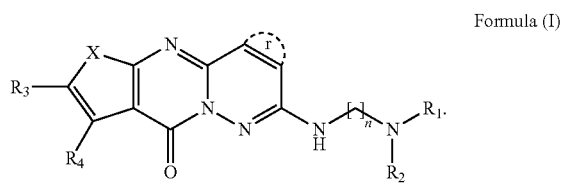

Formula (I)

$R^1$, $R^2$, $R^3$ and $R^4$ are each independently selected from hydrogen or a $C_1$-$C_3$-alkyl. The term "$C_1$-$C_3$ alkyl" as group used in the present invention refers to a hydrocarbyl radical having from 1 to 3 carbon atoms which includes a straight chain or branched alkyl group. Namely, it comprises methyl, ethyl, propyl and isopropyl. Likewise, "$C_1$-$C_2$ alkyl" refers to a hydrocarbyl radical in form of an alkyl having 1 to 2 carbon atoms.

In preferred embodiments, $R^1$, $R^2$, $R^3$ and $R^4$ are each independently selected from a $C_1$-$C_3$-alkyl. In further embodiments, $R^1$, $R^2$, $R^3$ and $R^4$ are each independently selected from hydrogen or a $C_1$-$C_2$-alkyl, further preferred from ethyl or methyl and in especially preferred embodiments of the present invention, $R^1$, $R^2$, $R^3$ and $R^4$ are all methyl.

r represents an optionally substituted $C_5$-$C_8$-aryl or optionally substituted $C_5$-$C_8$-heteroaryl, i.e. a $C_5$-$C_8$-aryl or $C_5$-$C_8$-heteroaryl which may optionally contain further substituents. As indicated in the Formula, the $C_5$-$C_8$-aryl or $C_5$-$C_8$-heteroaryl is fused to the backbone of the compound with two carbon atoms of the respective ring. "$C_5$-$C_8$-aryl" according to the invention means a cyclic hydrocarbon residue and hydrocarbyl radical, respectively, with 5 to 8 carbon atoms forming a ring with a maximum number of double bonds, i.e. with a maximum number of π electrons. "$C_5$-$C_8$-heteroaryl" according to the invention means a $C_5$-$C_8$-aryl in which at least one carbon atom has been replaced with a heteroatom, wherein heteroatoms are selected from O, S or N.

r is preferably an optionally substituted $C_5$-$C_8$-aryl. Still more preferably, r has the structure:

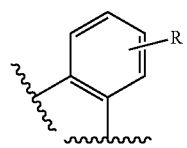

i.e. is an optionally substituted $C_6$-aryl. In said embodiments, R is hydrogen, a $C_1$-$C_2$ alkyl, $C_1$-$C_2$ alkoxy or a $C_1$-$C_2$ alkylamino. "$C_1$-$C_2$ alkylamino" refers to a radical having a formula —$NB_xH_y$, wherein x and y are selected from among x=1, y=1 and x=2, y=0 and B is a $C_1$-$C_2$ alkyl, i.e. the number of carbon atoms in B is 1 to 2. "$C_1$-$C_2$ alkoxy" refers to a radical having a formula -AB wherein A is an oxygen atom and B is $C_1$-$C_2$ alkyl, i.e. including methoxy and ethoxy. Most preferably, R is hydrogen. Accordingly, in especially preferred embodiments of the present invention, r is an unsubstituted $C_6$-aryl, i.e. unsubstituted benzene ring.

n is an integer indicating the number of methylene groups and is of from 1 to 5, more preferably selected from 1, 2, 3 or 4, further preferred from 2, 3 or 4 and in particular embodiments of the present invention, n is 3. For example, if n is 1, there is one methylene group present at the respective position.

X is a heteroatom and selected from N, O or S. In more preferred embodiments of the present invention, X is S.

Contemplated by the present invention is the base or any protonated form of the compound of Formula (I). Also contemplated by the present invention is any pharmaceutically acceptable salt, anhydrate or solvate of the compound of Formula (I).

As used herein, the term "solvate" refers to a complex of variable stoichiometry formed by a solute, i.e. compound of Formula (I), and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical composition.

Said compound of Formula (I) is, among others, characterized by certain structural elements, which were found to unexpectedly contribute to an advantageous inhibition of the activity of the ALK kinase by interacting with amino acids within the ALK kinase domain and ALK binding pocket, respectively. Namely the compound of the present invention comprises a tricyclic heteroaromatic ring system in the backbone, at least one tertiary amine in the side chain attached via a secondary nitrogen containing and at most 6-membered linking group as well as a hydrophobic moiety fused to the backbone referenced as r. Further moieties which may be attached to the backbone or side chain according to Formula (I) do not impede the interaction with the ALK kinase domain and preferably allow for additional interactions including van der Waals forces and hydrogen bonds or hydrophobic interactions with the ALK kinase domain and, thus, further contribute to the exceptional interaction with the ALK kinase.

The inventors unexpectedly found that the presence of these structural components allows for advantageous and multiple interactions with the ALK kinase domain by means of hydrophobic interactions due to the hydrophobic ring structures and groups in the compound of Formula (I) and polar interactions due to the presence of highly electronegative atoms including hydrogen bonds such as with residues L1122 and E1210 in the ALK binding pocket formed by the secondary and tertiary amine in the side chain. These interactions are considered for being important ones allowing for the advantageous interaction with the ALK kinase domain and a potent inhibition of the activity of ALK kinase and, hence, ALK fusion kinases as said ALK kinase domain is fully retained in known fusion partners, i.e. in known ALK fusion kinases.

In especially preferred embodiments, the compound is a compound of Formula (II):

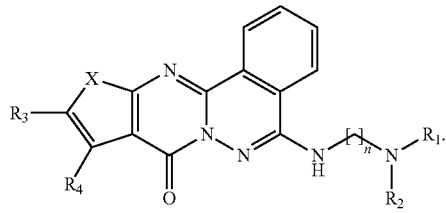

Formula (II)

$R^1$, $R^2$, $R^3$ and $R^4$ are each independently selected from hydrogen or a $C_1$-$C_2$-alkyl. In especially preferred embodiments of the present invention, $R^1$, $R^2$, $R^3$ and $R^4$ are independently selected from ethyl or methyl and in particular embodiments, they are all methyl.

X is a heteroatom and selected from N, O or S. In more preferred embodiments of the present invention, X is S.

n is selected from 1, 2, 3 or 4, further preferred from 2, 3 or 4 and in particular embodiments of the present invention, n is 3.

In particular embodiments of the present invention, the compound is a compound of Formula (III):

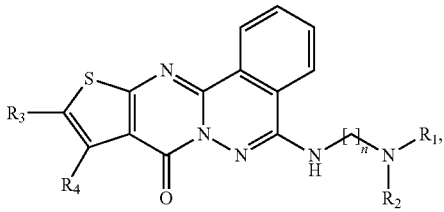

Formula (III)

with $R^1$, $R^2$, $R^3$ and $R^4$ being independently selected from hydrogen or a $C_1$-$C_2$-alkyl, preferably independently selected from ethyl or methyl and in particular, they are all methyl. n is selected from 2, 3 or 4 and in more preferred embodiments of the present invention, n is 3.

In particular embodiments of the present invention, the compound is of Formula (IV) including any protonated form thereof, in particular it is of Formula (V):

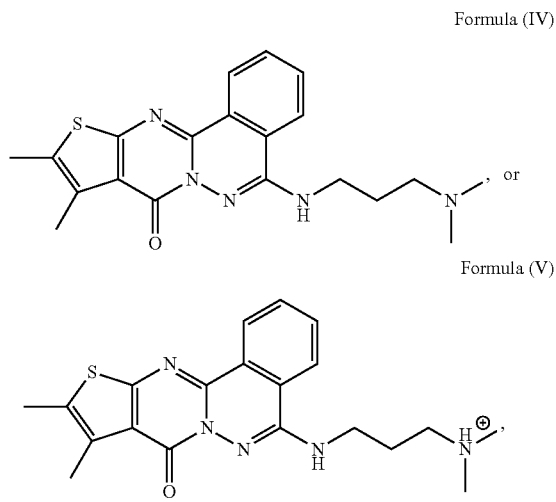

Formula (IV)

Formula (V)

which is also referenced as "5067-0952" herein and includes any pharmaceutically acceptable salt, solvate or anhydrate thereof.

As further shown below, respective data with H2228 cell lines with ALK chromosome rearrangement further confirm that compound of Formula (V) is particular effective in inhibiting ALK kinase activity. The compound of Formula (V) proved to be highly cytotoxic and selective against cancer cells. It proved to advantageously target ALK fusion kinase, respectively, while showing relatively low toxicity to normal lung cells. In particular, the compound of Formula (V) proved to exceptionally inhibit growth, induce apoptosis and suppress the phosphorylation of ALK fusion kinase while making use of the NSCLC cell line H2228, which is a NSCLC cell line characterized by the ALK rearrangement EML4-ALK (variant 3).

The expression "effective amount" generally denotes an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells, in particular inhibition, reduction or prevention of the proliferation of the cancer cells or induction of cell death, i.e. apoptosis of the cancer cells.

The effective amount of the compound of Formula (I) may depend on the species, body weight, age and individual conditions and can be determined by standard procedures such as with cell cultures or experimental animals. The concentration of the compound of Formula (I), such as the compound of Formula (V), effective for treating the subject may, for example, be at least 5 µM or at least 10 µM.

Preferably, the compound of Formula (I) has an $IC_{50}$ on cancer cells of at most 10 µM, further preferred of at most 8 µM and further preferred at most 6 µM, and an $IC_{50}$ on normal non-cancerous cells being at least 1.5, further preferred at least 2 times higher, more preferably at least 2.5 times higher, most preferably at least 3 times higher than the $IC_{50}$ on cancer cells.

In embodiments of the present invention, the disease is an ALK-dependent NSCLC, wherein the abnormality in the ALK gene is an ALK chromosome rearrangement selected from one or more of EML4-ALK, KIF5B-ALK, KLC1-ALK, PTPN3-ALK, STRN-ALK and TFG-ALK, most preferably EML4-ALK, and the compound has an $IC_{50}$ on said NSCLC cells of at most 8 µM such as at most 6 µM and an $IC_{50}$ on normal lung cells being at least 2 times higher than the $IC_{50}$ on said NSCLC cells.

In still further embodiments of the present invention, the compound is a compound of Formula (IV) in particular of Formula (V) and the disease is ALK-dependent NSCLC, wherein the abnormality in ALK gene is an ALK chromosome rearrangement selected from EML4-ALK including respective variants.

The method of the present invention may further include steps carried out before administering the compound of Formula (I), such as compound of Formula (IV) and in particular of Formula (V), to the subject comprising:

Obtaining a sample, in particular cancer cells, from the subject;

Testing said sample for the level of expression of ALK kinase, in particular of at least one ALK fusion kinase or identifying at least one ALK chromosome rearrangement;

Optionally correlating the level of expression of the ALK kinase or presence of an ALK chromosome rearrangement with outcome and if conditions are met, administrating the compound of Formula (I), in particular compound of Formula (IV) such as of Formula (V), to said subject.

According to the invention is also the compound of Formula (I), in particular the compound of Formula (IV) such as of Formula (V), for use as a medicament, preferably for use in the treatment of cancer such as lung cancer, especially NSCLC, in particular ALK-dependent cancer, especially ALK-dependent NSCLC. The compound of Formula (I), in particular the compound of Formula (IV) such as of Formula (V), can be used in an effective amount for treating a human. Another aspect of the invention refers to the use of the compound of Formula (I), in particular the compound of Formula (IV) such as of Formula (V), for preparing a medicament for treatment of a disease, in particular of cancer, especially lung cancer, in particular NSCLC, especially ALK-dependent NSCLC.

The compound of Formula (I) may be administered in form of a pharmaceutical composition comprising the compound of Formula (I) and at least one pharmaceutically acceptable excipient. The compound of Formula (I) may be administered in combination with other therapeutic compounds, preferably therapeutic compounds which are used for treating cancer such as lung cancer, especially NSCLC.

In still another aspect, the present invention refers to a method of inhibiting ALK kinase activity, in particular ALK fusion kinase activity, in cancer cells by a compound of Formula (I) in a subject in need thereof, i.e. comprising administering an effective amount of a compound of Formula (I)

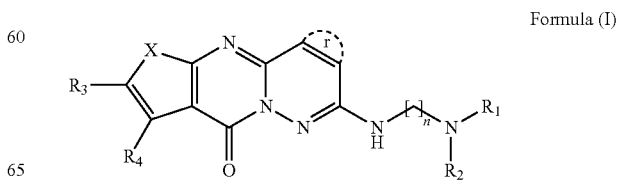

Formula (I)

to a subject suffering from cancer, in particular lung cancer like NSCLC. $R_1$ to $R_4$, n, r and X are as defined above including preferred embodiments described above. In preferred embodiments of the present invention, the cancer is ALK-dependent NSCLC, preferably from an NSCLC adenocarcinoma.

The concentration of the compound of Formula (I) effective for inhibiting ALK kinase activity may, for example, be at least 5 μM or at least 10 μM. Preferably, the compound of Formula (I) has an $IC_{50}$ on cancer cells of at most 10 μM, further preferred of at most 8 μM and further preferred at most 6 μM, and an $IC_{50}$ on normal non-cancerous cells being at least 1.5 times higher, further preferred at least 2 times higher, more preferably at least 2.5 times higher, most preferably at least 3 times higher than the $IC_{50}$ on cancer cells.

In embodiments of the present invention, the cancer is an ALK-dependent NSCLC, wherein the abnormality in the ALK gene is an ALK chromosome rearrangement selected from one or more of EML4-ALK, KIF5B-ALK, KLC1-ALK, PTPN3-ALK, STRN-ALK and TFG-ALK, most preferably EML4-ALK including respective variants, namely including EML4-ALK, E13;A20 (variant 1), EML4-ALK, E20;A20 (variant 2), EML4-ALK, E6a/b;A20 (variant 3a/b), EML4-ALK, E14;A20 (variant 4), EML4-ALK, E2a/b;A20 (variant 5a/b), EML4-ALK, E13b;A20 (variant 6), EML4-ALK, E14;A20 (variant 7), EML4-ALK, E15;A20 (variant "V4"), EML4-ALK, E17;A20 and EML4-ALK, E18;A20 (variant "V5"), in particular from EML4-ALK, E13;A20 (variant 1), EML4-ALK, E20;A20 (variant 2) or EML4-ALK, E6a/b;A20 (variant 3a/b). Preferably, the ALK kinase which activity is inhibited comprises or is at least one ALK fusion kinase resulting from an EML4-ALK chromosome rearrangement, in particular from EML4-ALK, E13;A20 (variant 1), EML4-ALK, E20;A20 (variant 2) or EML4-ALK, E6a/b;A20 (variant 3a/b).

In particular embodiments, the compound administered for inhibiting ALK kinase activity, in particular ALK fusion kinase activity resulting from a chromosome rearrangement preferably selected from one or more of EML4-ALK, KIF5B-ALK, KLC1-ALK, PTPN3-ALK, STRN-ALK and TFG-ALK, most preferably EML4-ALK, is of Formula (IV) and in particular is the protonated form of Formula (V):

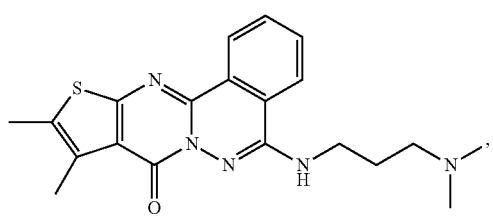

Formula (IV)

in particular

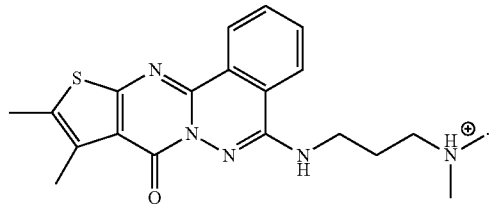

Formula (V)

In particular, the method is for inhibiting phosphorylation of ALK kinase, in particular ALK fusion kinase, and/or for inhibiting the anti-apoptotic and growth signaling downstream to ALK kinase, in particular to ALK fusion kinase, by means of inhibiting ALK kinase activity. In particular, the method is for inhibiting, reducing or preventing the proliferation of the cancer cells or inducing apoptosis of the cancer cells by means of inhibiting ALK kinase activity.

A further aspect of the present invention relates to a composition comprising the compound of Formula (I) or a salt, solvate or anhydrate thereof:

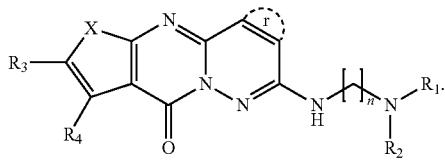

Formula (I)

$R_1$ to $R_4$, n, r and X are as defined above including preferred embodiments as described above. The composition further comprises excipients such as pharmaceutically acceptable excipients, a buffer, salt, water or a combination thereof. In particular the composition is a pharmaceutical composition comprising the compound of Formula (I) or a pharmaceutically acceptable salt, solvate or anhydrate thereof. Said pharmaceutical composition further comprises pharmaceutically acceptable excipients and may additionally contain further active ingredients, in particular therapeutic compounds for treating cancer such as NSCLC.

The skilled person is able to select suitable excipients depending on the form of the pharmaceutical composition and is aware of methods for manufacturing pharmaceutical compositions as well as able to select a suitable method for preparing the pharmaceutical composition depending on the kind of excipients and the form of the pharmaceutical composition. The pharmaceutical composition according to the invention can be present in solid, semisolid or liquid form to be administered by an oral, rectal, topical, parenteral or transdermal or inhalative route to a subject, preferably a human.

Most preferably, the compound in the composition is a compound of Formula (IV):

Formula (IV)

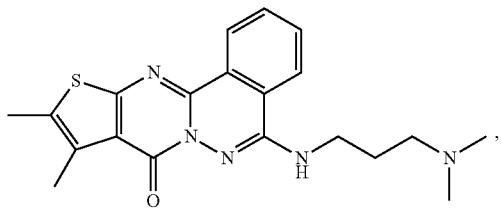

including any protonated form thereof, in particular it is of

Formula (V)

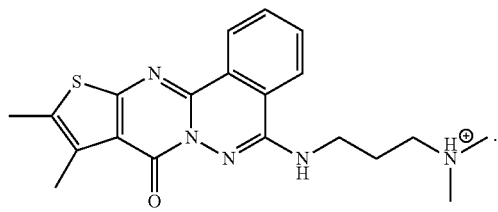

The present invention also refers to the use of the composition such as the pharmaceutical composition for inhibiting ALK kinase activity, in particular ALK fusion kinase activity, such as for suppressing phosphorylation of ALK kinase, in particular ALK fusion kinase, and/or inhibiting the anti-apoptotic and growth signaling downstream to ALK kinase, in particular to ALK fusion kinase.

The present invention in another aspect refers to a method for targeting cancer cells harboring an abnormality in ALK gene. Said abnormality in ALK gene is preferably an ALK chromosome rearrangement, preferably the cancer cells express at least one ALK fusion kinase resulting from an EML4-ALK chromosome rearrangement, in particular from EML4-ALK, E13;A20 (variant 1), EML4-ALK, E20;A20 (variant 2) or EML4-ALK, E6a/b;A20 (variant 3a/b). The cancer cells are preferably from a lung cancer, more preferably from a NSCLC in particular from an NSCLC adenocarcinoma.

Said method of the present invention comprises the step of contacting said cells such as in a sample or tissue comprising said cells with a compound of Formula (I) or a salt, solvate or anhydrate thereof:

Formula (I)

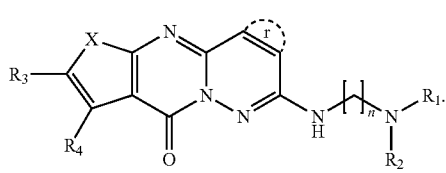

$R_1$ to $R_4$, n, r and X are as defined above including preferred embodiments as described above.

Preferably, the proliferation of the cancer cells is inhibited, reduced or prevented or apoptosis of the cancer cells is induced. The skilled person is aware of methods for verifying such effects such as with cell viability measurement by means of a MTS proliferation assay, a MTT assay or by determination of the apoptosis rate by means of Annexin V flow cytometry measurement.

Preferably, the cancer cells are contacted with the compound of Formula (I) for at least 12 h, more preferably for at least 24 h and in particular for about 72 h. The compound of Formula (I) is preferably used in a concentration of at least 2.5 µM, further preferred at least 5 µM and more preferably at least 10 µM. The cancer cells contacted with the compound of Formula (I) may comprise, for example, $1.0 \times 10^2$ cells to $1.0 \times 10^6$ cells per well such as about $1.0 \times 10^3$ cells, about $3.0 \times 10^3$ cells or about $2.0 \times 10^5$ cells per well.

The compound of Formula (I) has an $IC_{50}$ on cancer cells of at most 10 µM, in particular at most 8 µM such as at most 6 µM and an $IC_{50}$ on normal non-cancerous cells being at least 1.5 times higher, preferably at least 2 times higher, more preferably at least 2.5 times higher and in particular at least 3 times higher than the $IC_{50}$ on said cancer cells. In preferred embodiments of the present invention, the compound has an $EC_{50}$ of at most 30 nM and an $IC_{50}$ on the cancer cells of at most 6 µM.

In embodiments of the present invention, the cancer cells are from NSCLC and harbor an abnormality in ALK gene being an ALK chromosome rearrangement selected from one or more of EML4-ALK, KIF5B-ALK, KLC1-ALK, PTPN3-ALK, STRN-ALK and TFG-ALK, most preferably EML4-ALK, and the compound has an $IC_{50}$ on the cancer cells of at most 8 µM, preferably at most 6 µM and an $IC_{50}$ on normal non-cancerous lung cells being at least 2 times higher than the $IC_{50}$ on said cancer cells.

Preferably, the compound used for contacting the cancer cells is a compound of Formula (III) or a salt, solvate or anhydrate thereof:

Formula (III)

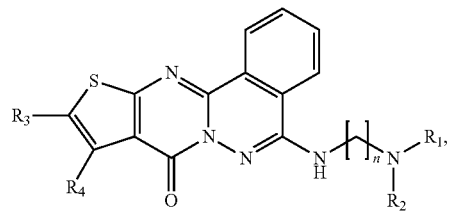

wherein the concentration of the compound of Formula (III) for contacting the cells is at least 2.5 µM. $R^1$, $R^2$, $R^3$ and $R^4$ are independently selected from hydrogen or a $C_1$-$C_2$-alkyl, preferably independently selected from ethyl or methyl and in particular, they are all methyl. n is selected from 2, 3 or 4 and in more preferred embodiments of the present invention, n is 3.

In particular embodiments of the present invention, the compound used for contacting said cells is a compound having Formula (IV) or a salt, solvate or anhydrate thereof:

Formula (IV)

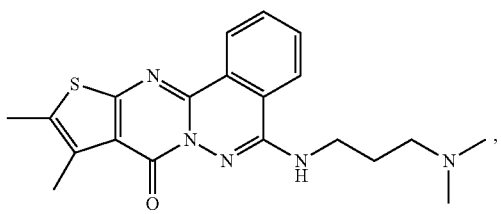

such as a protonated form thereof, in particular

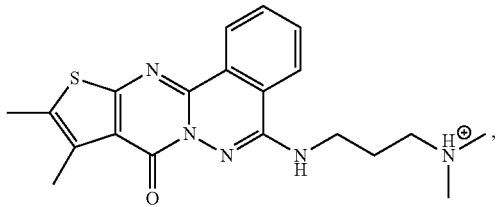

Formula (V)

wherein the concentration of the compound of Formula (IV), in particular Formula (V), for contacting the cells is at least 5 μM, further preferably at least 10 μM.

The skilled person is able to prepare the compound of Formula (I) with suitable purity and/or respective compounds are commercially available with sufficient purity.

EXAMPLES

Example 1

Binding Mode Between the Compound of Formula (V) and ALK Kinase

The binding mode of ALK with the compound of Formula (V) was analyzed using molecular docking method. The 3D structure of the compound of Formula (V) was obtained from the Chemdiv database. Then, the inhibitor was preprocessed and optimized by the LigPrepmodule with OPLS-2005 force field. The ionized state was assigned by using Epik at a target pH value of 7.0±2.0. The 3D crystal structure of the Anaplastic Lymphoma Kinase (ALK) for molecular docking was retrieved from the Protein Data Bank (PDB ID code 2XP2). The Protein Preparation Wizard was used to remove crystallographic water molecules, add hydrogen atoms, assign partial charges. The compound of Formula (V) was docked into the binding site of the ALK using the Glide docking program with the standard precision (SP) scoring mode. The docking grid box was defined by centering on the crizotinib in the ALK. In molecular docking, 500 poses were generated during the initial phase of the docking calculation, out of which best 100 poses were chosen for energy minimization by 1000 steps of conjugate gradient minimizations.

FIG. 1 illustrates the structure of the compound of Formula (V) docked into the predicted binding site of ALK. As can be seen in FIG. 1, the interactions between ALK and the compound of Formula (V) consist of hydrophobic, polar and hydrogen bond interactions. The hydrophobic groups of the compound of Formula (V) form hydrophobic interactions with the side chain of V1130, K1150, M1199 and L1256. The polar group of the compound of Formula (V) has polar interaction with the side chain of L1122, E1197, D1203 and E1210. The compound of Formula (V) also forms hydrogen bonds with the side chain of L1122 and E1210.

Example 2

Inhibition of ALK Kinase

Further, the efficiency of the compound of Formula (V) as inhibitor of ALK kinase has been evaluated including its cytotoxic properties and selectivity towards cancer cells with ALK chromosome rearrangement, its efficacy in inducing cell deaths and inhibition of colony formation in those cells as well as the effects on the ALK phosphorylation and anti-apoptotic and growth signaling pathways downstream to ALK.

Crizotinib was purchased from Selleck Chemicals. The compound of Formula (V) was purchased from ChemDiv. They were dissolved in DMSO to a 10 mM or 20 mM concentration and stored in small aliquots at −20° C. until further use. Antibodies to GAPDH, ALK, p-ALK (1282/1283), p-AKT (Ser473), p-ERK (Thr202/Thy204), ERK, p-STAT3 and STAT3 were purchased from Cell signaling Technology.

H2228 and CCD19(Lu) cells were obtained from the American Type Culture Collection and cultured in an environment of 5% $CO_2$ at 37° C. in RPMI-1640 mediums supplemented with 10% fetal bovine serum (FBS), 100 units/mL penicillin, and 100 μg/mL streptomycin.

Descriptive analytical data were presented as means±SEM. Multiple comparisons were evaluated by one-way analysis of variance (ANOVA) followed by using Graph Prim5.0. Values of $P<0.05$ were considered statistically significant.

Example 2A

Enzyme Inhibitory Activity of the Compound of Formula (V) on ALK

Enzymatic assay for recombinant ALK kinase domain was conducted using the LanthaScreen® Eu Kinase Binding Assays. LanthaScreen® Eu Kinase Binding Assays are based on the binding and displacement of a proprietary. The assay was performed at room temperature for 1 h in a total volume of 15 μL, including 5 μL of test compound, 5 μL of kinase/antibody mixture and 5 μL of tracer. After 1 h incubation, fluorescence was measured. The division of acceptor/tracer emission (665 nm) by the antibody/donor emission (615 nm) was used to calculate the emission ratio.

The in-vitro enzymatic activity assay to assess binding capacity between the compound of Formula (V) and ALK revealed an $EC_{50}$ of the compound of Formula (V) for recombinant ALK kinase activity of 19.63 nM, although it is higher than crizotinib, it has exceptional ALK kinase inhibition activity.

Example 2B

Cytotoxic Effects of the Compound of Formula (V) Towards Cells with ALK Chromosome Rearrangement Cell viability was determined by MTT assay. H2228 and CCD19 cells ($3 \times 10^3$ cells/well) were seeded into a 96-well plate and treated with indicated concentrations of the compound of Formula (V) for 72 h. At the end of incubation, 10 μl MTT (0.5 mg/ml) (Sigma) was added to each well. After incubating for 4 h at 37° C., supernatants were removed and 150 μl of DMSO was added. The formazan crystals formed inside the viable cells were solubilized in DMSO and the OD was read with Microplate Reader (Epoch, Winooski, USA) at 570 nm. The $IC_{50}$ value for the compound was determined by GraphPad Prim5.0 software. The experiments were performed three times with three replicates in each.

Figure 3A:
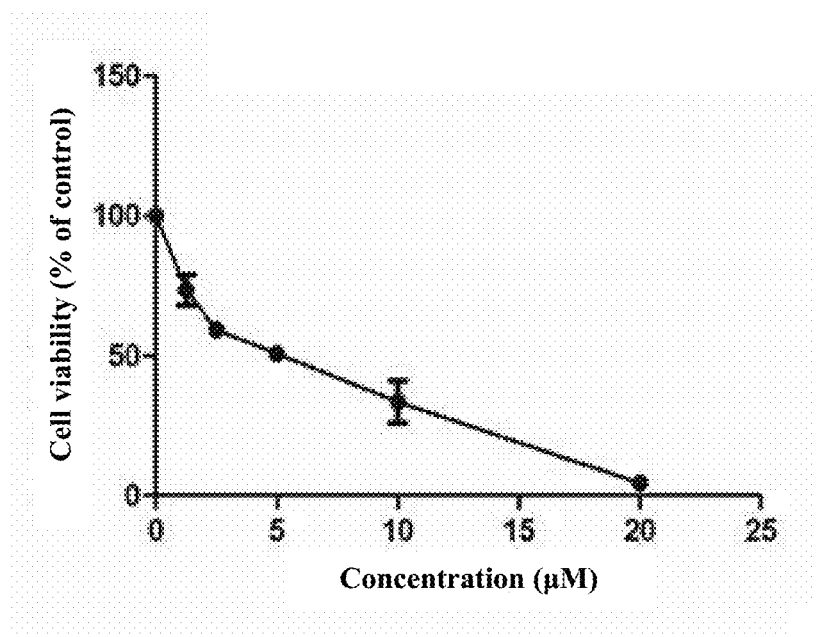
FIGS. 3A and 3B show the cytotoxicity of the compound of Formula (V).
Figure 3B:
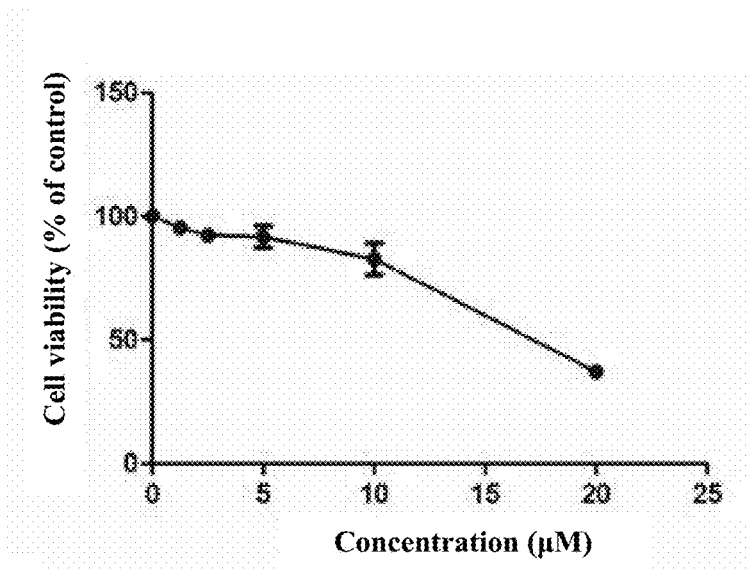
Figure 4A:
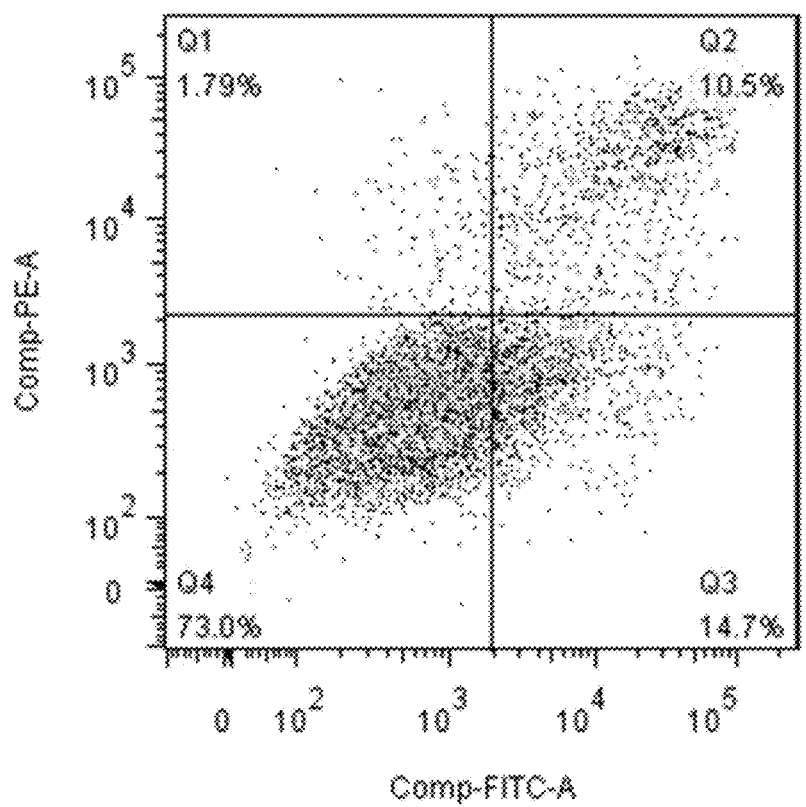
FIGS. 4A, 4B, 4C, 4D, and 4E show Flow Cytometry patterns of H2228 cells having been treated with different concentrations of the compound of Formula (V) of the present invention, with crizotinib or of the control group.
Figure 4B:
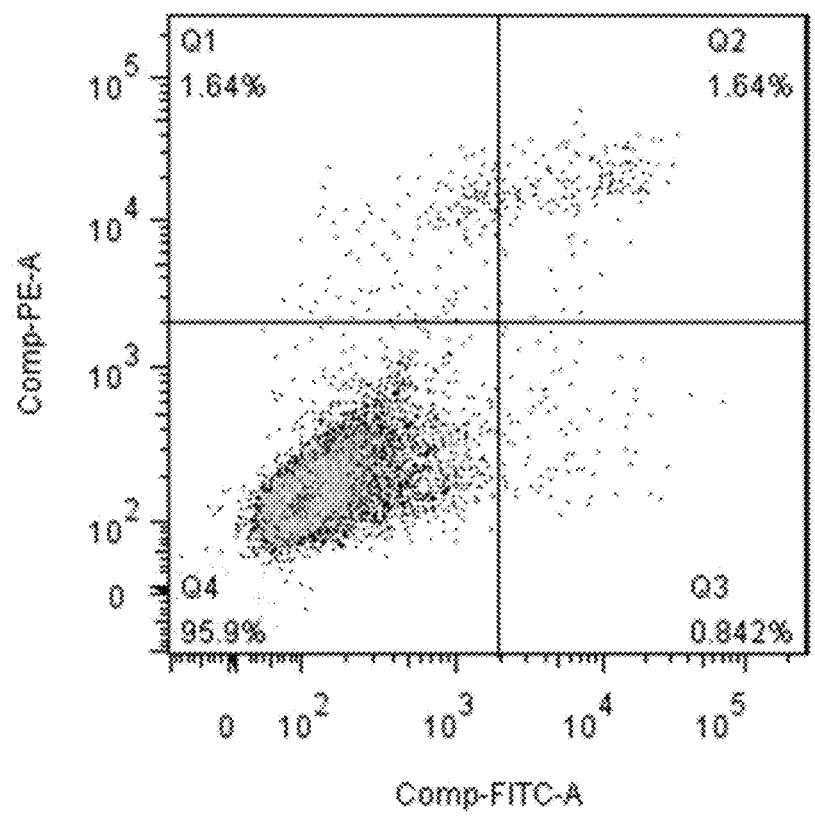
Figure 4C:
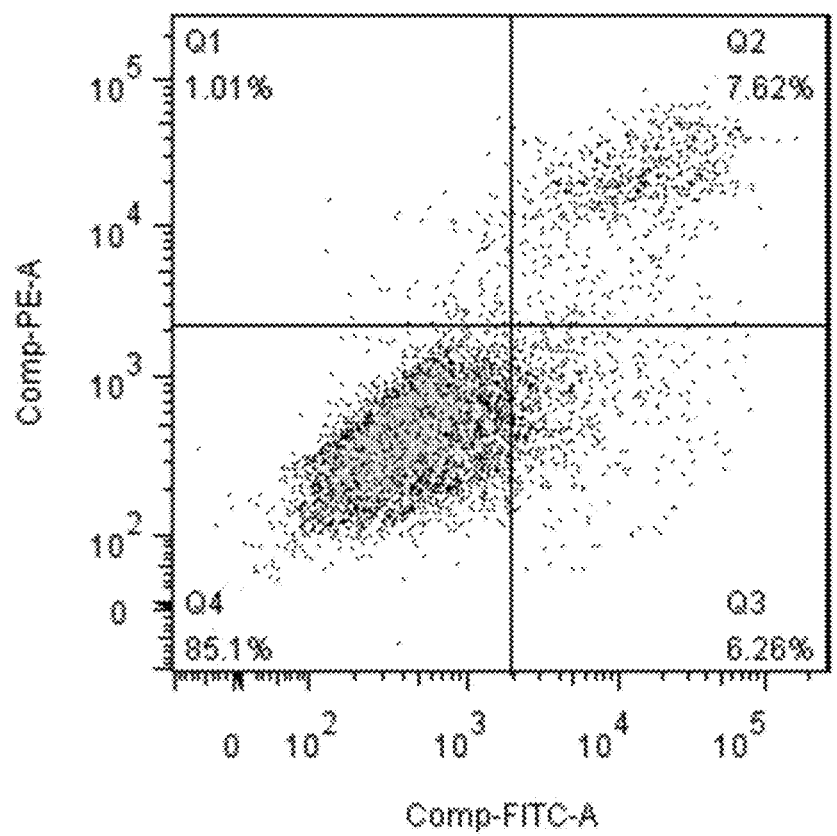
Figure 4D:
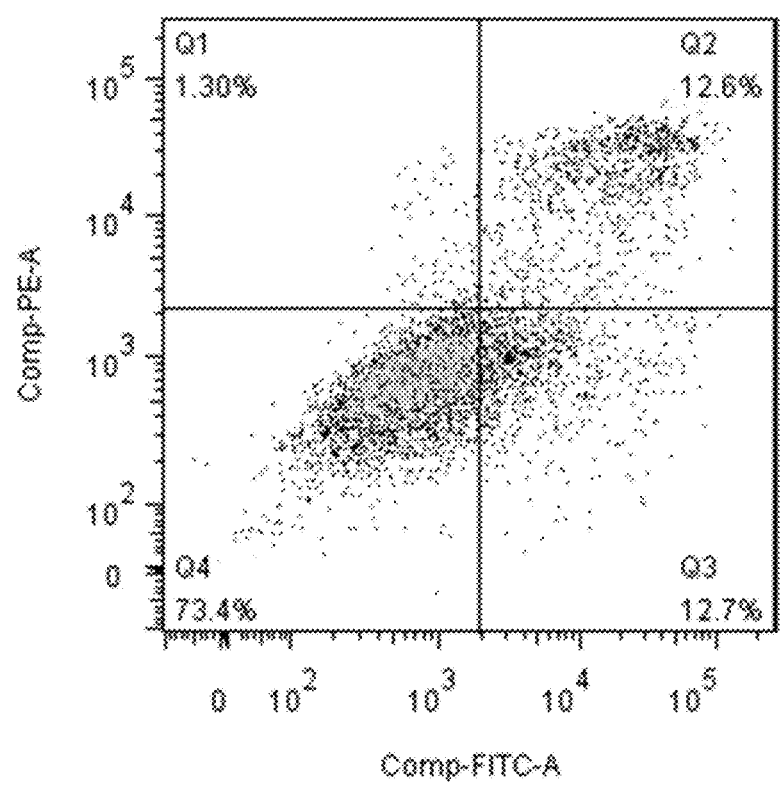
Figure 4E:
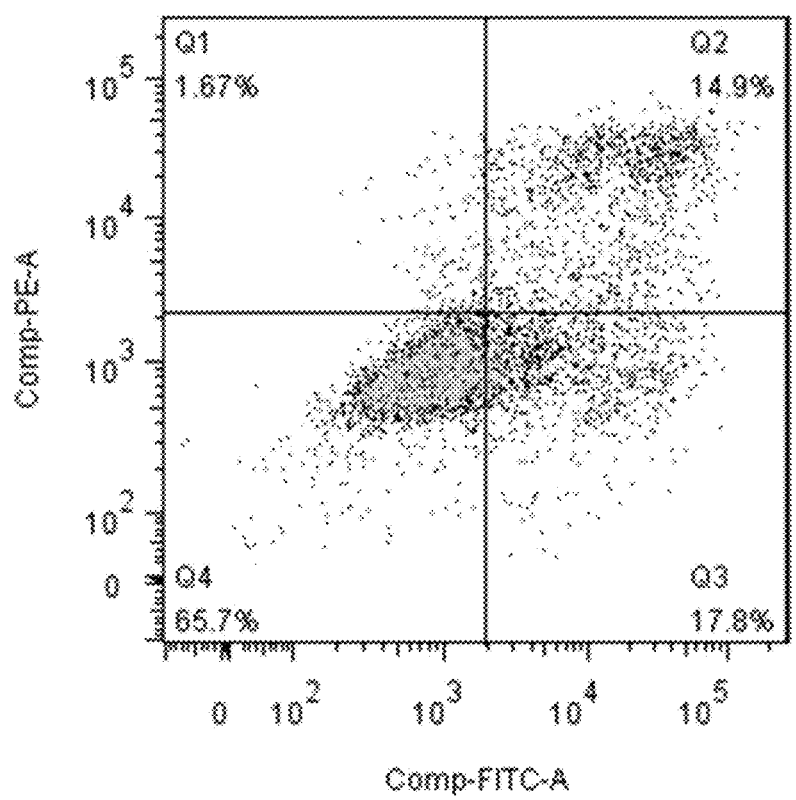
Figure 4F:
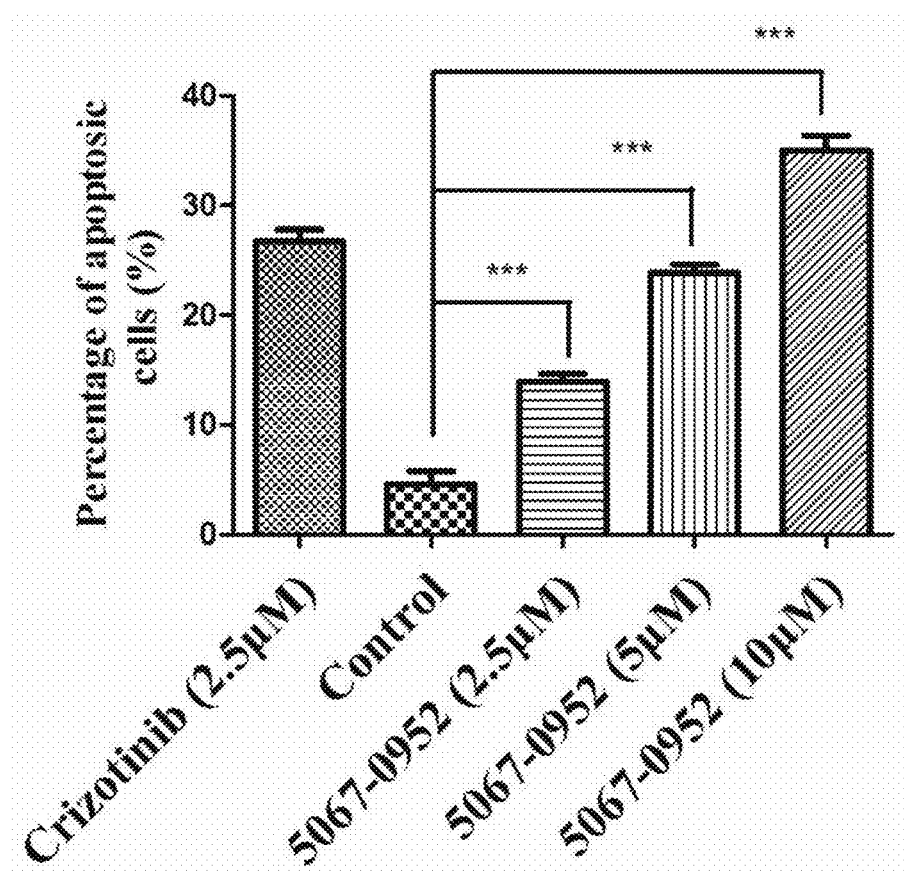
FIG. 4F shows the rate of apoptosis of H2228 cells having been treated with the compound of Formula (V) (referenced as "5067-0952") of the present invention with 2.5 µM, 5 µM or 10 µM or with 2.5 µM crizotinib compared to the control group.
Figure 5A:
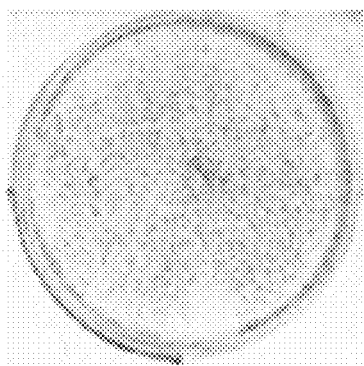
FIGS. 5A, 5B, 5C, 5D, and 5E show the formation of H2228 cell colonies after treatment with different concentrations of the compound of Formula (V), crizotinib or of the control group.
Figure 5B:
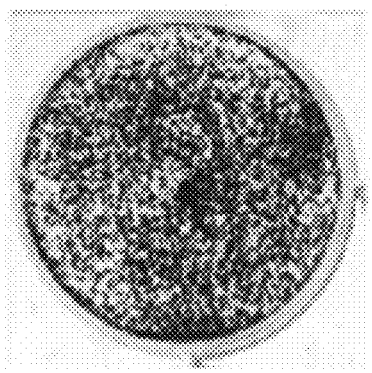
Figure 5C:
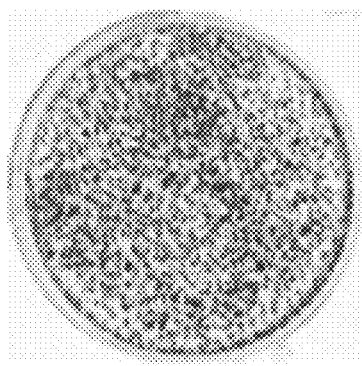
Figure 5D:
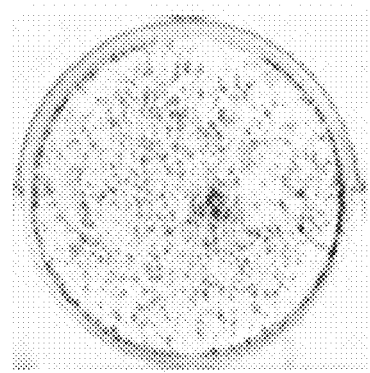
Figure 5E:
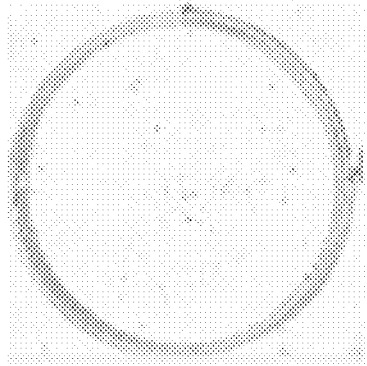

MTT assay showed that treatment with the compound of Formula (V) significantly decreased cell viability in a concentration-dependent manner, with the $IC_{50}$ value as indicated in table 1 and a lower cytotoxicity on normal lung cells CCD19 (see FIGS. 3A and 3B).

TABLE 1

IC$_{50}$ of the compound of Formula (V)

| Cell line | IC$_{50}$ (μM) |
|---|---|
| H2228 | 4.11 ± 0.96 |
| CCD19 | 16.81 ± 2.04 |

Example 2C

Induction of Apoptosis in H2228 Cells by the Compound of Formula (V)

Cells (2×10$^5$) were seeded in a six-well plate and cultured overnight for cell adhesion, and treated with indicated concentrations of the compound of Formula (V) for 48 h, the cells were washed with PBS and detached with trypsin, then cells were resuspended in 100 μL of staining solution (containing 5 μL Annexin V-FITC and 5 μL PI in Binding Buffer), followed by staining at room temperature in the dark for 15 min. 400 μL of chilled binding buffer was added and mixed gently prior to the examination of the cell preparations by flow cytometry (FACSCalibur; BD Biosciences, San Jose, Calif., USA).

Flow cytometry analysis showed that the decrease in cell viability by the compound of Formula (V) was caused in part by induction of apoptosis on H2228 cells in a concentration-dependent manner. Compared with the control group, treatment on H2228 cells with the compound of Formula (V) induced significant levels of cell apoptosis (see FIG. 4A to 4F).

Example 2D

Suppression of Colony Formation of H2228 Cells by the Compound of Formula (V)

H2228 cells (1.0×10$^3$ cells/well) were seeded in 6-well plate, after attachment overnight, the compound was added and cells were exposed for two weeks to form clones. The cells were washed with PBS, fixed with 4% paraformaldehyde for 20 min, and stained with crystal violet (1% paraformaldehyde, 0.5% crystal violet, and 20% methanol in ddH$_2$O) for 20 min. The clone numbers on each plate were counted to measure cell survival ability. Colonies with more than 50 cells were counted as colony-forming units.

Colony formation assay demonstrated that the compound of Formula (V) shows great efficacy in blocking colony formation of H2228 cell colonies in a dose-dependent manner, notably, when the compound of Formula (V) concentration reached 10 μM, H2228 cells formed no visible colonies (see FIG. 5A to 5E).

Example 2E

Suppression of ALK Phosphorylation and Anti-Apoptotic and Growth Signaling Pathways Downstream to ALK by the Compound of Formula (V)

Cells were lysed in modified RIPA buffer (50 mM Tris pH 7.4, 150 mM NaCl, 1% NP-40, 1 mM EDTA, 0.25% sodium deoxycholate) containing protease inhibitors. Lysates were centrifuged at 14,000×g at 4° C. for 10 min. Protein concentrations of the lysates were determined by the Bradford protein assay system (Bio-Rad, Hercules, Calif.). Equal amounts of protein (30 μg protein each lane) were separated by SDS-PAGE, transferred to nitrocellulose membranes (Hybond C, Amersham, UK). Immunoblots were blocked with 5% skim milk in TBS/Tween 20 (0.05%, v/v) for 1 hour at room temperature, followed by overnight incubation at 4° C. with primary antibodies. After washing 3 times by TBST, the membranes were incubated with secondary rabbit or mouse fluorescent antibodies, then the signal intensity of the membranes was detected by anLI-COR Odessy scanner (Belfast, Me., USA). All primary antibodies were diluted at 1:1000, while their recommended secondary antibodies were diluted at 1:10000.

Figure 6:
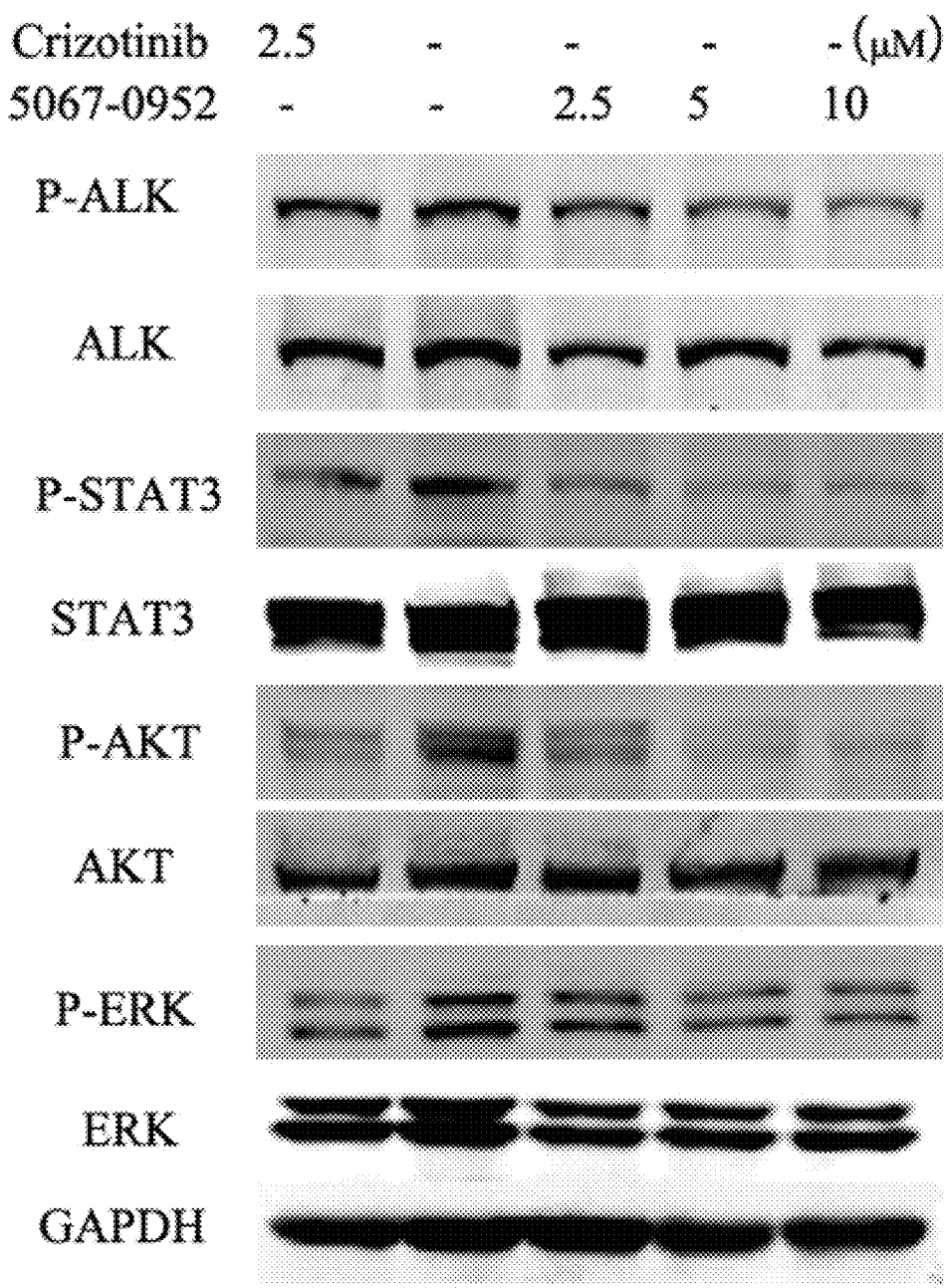
FIG. 6 refers to a western blot and shows the expression of phosphorylated ALK, ALK, phosphorylated STAT3, STAT3, phosphorylated AKT, AKT, phosphorylated ERK, ERK and GAPDH of a control group and H2228 cells treated with 2.5 µM crizotinib or with 2.5 µM, 5 µM or 10 µM of the compound of Formula (V) (referenced as "5067-0952").

The anti-tumor efficacy of the compound of Formula (V) was dose-dependent and led to an exceptional suppression of ALK phosphorylation. Strong downregulation of ERK, AKT and STAT3 phosphorylation was also seen in H2228 cells in response to the compound of Formula (V) (see FIG. 6).

The invention claimed is:

1. A method of inhibiting ALK kinase activity in ALK-dependent non-small cell lung cancer cells comprising administering an effective amount of a compound of Formula (II) or a pharmaceutically acceptable salt, solvate or anhydrate thereof to a subject suffering from ALK-dependent non-small cell lung cancer:

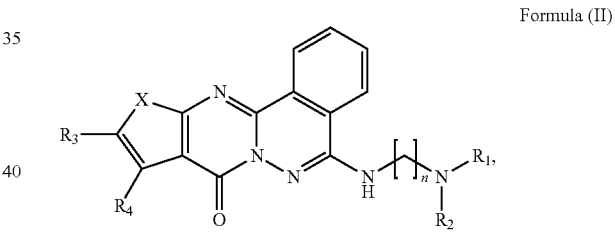

Formula (II)

wherein:
R$^1$, R$^2$, R$^3$ and R$^4$ are each independently selected from hydrogen or a C$_1$-C$_2$-alkyl;
n is an integer selected from 1, 2, 3 and 4; and
X is a heteroatom selected from N, O and S.

2. The method of claim 1, wherein the compound is a compound of Formula (IV):

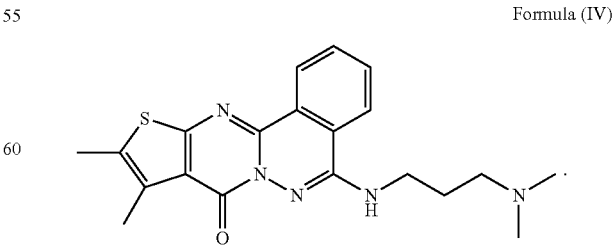

Formula (IV)

3. The method of claim 1, wherein the compound is a compound of Formula (V):

Formula (V)

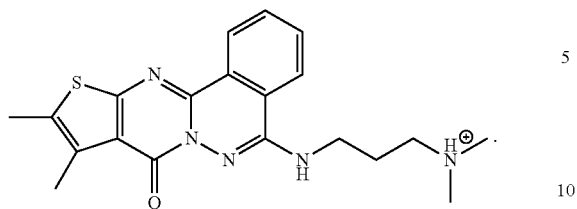

4. The method of claim 1, wherein the subject is a human and the ALK-dependent non-small cell lung cancer includes cancer cells with an abnormality in ALK gene, which abnormality in ALK gene results from an ALK chromosome rearrangement selected from the group consisting of EML4-ALK, KIF5B-ALK, KLC1-ALK, PTPN3-ALK, STRN-ALK and TFG-ALK.

5. The method of claim 4, wherein the abnormality in ALK gene results from an EML4-ALK chromosome rearrangement.

* * * * *